US011739045B1

(12) United States Patent
Bristow

(10) Patent No.: US 11,739,045 B1
(45) Date of Patent: Aug. 29, 2023

(54) CRYSTAL OF TEFLUTHRIN, PREPARATION METHOD THEREFOR AND USE THEREOF

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 17/676,969

(22) Filed: Feb. 22, 2022

(51) Int. Cl.
*C07C 61/40* (2006.01)

(52) U.S. Cl.
CPC .......... *C07C 61/40* (2013.01); *C07B 2200/13* (2013.01)

(58) Field of Classification Search
CPC ............................ C07C 61/40; C07B 2200/13
See application file for complete search history.

(56) References Cited

FOREIGN PATENT DOCUMENTS

CN 1760168 * 4/2006

OTHER PUBLICATIONS

CN1760168 translated (Year: 2006).*

* cited by examiner

*Primary Examiner* — Yevgeny Valenrod
*Assistant Examiner* — Blaine G Doletski
(74) *Attorney, Agent, or Firm* — Dickinson Wright PLLC

(57) ABSTRACT

The present invention belongs to the technical field of fine chemicals and relates to a new crystalline form of tefluthrin, a preparation method therefor and the use thereof. The preparation method specifically comprises: taking an amorphous tefluthrin or a solid tefluthrin other than the tefluthrin as described in the present invention as a raw material, firstly preparing the raw material into an amorphous substance at room temperature, and then allowing the amorphous substance to cool to 5° C. to −24° C. to obtain a white or light yellow solid, i.e., a new crystalline form of tefluthrin.

12 Claims, 3 Drawing Sheets

CRYSTAL OF TEFLUTHRIN, PREPARATION METHOD THEREFOR AND USE THEREOF

TECHNICAL FIELD

The present invention relates to fine chemicals and specifically relates to a new crystalline form of 2,3,5,6-tetrafluoro-4-methylbenzyl-(1RS,3RS)-3-[(Z)-2-chloro-3,3,3-trifluoroprop-1-enyl]-2,2-dimethylcyclopropane carboxylate (tefluthrin), a preparation method therefor and the use thereof in an agrochemical preparation.

BACKGROUND ART 2,3,5,6-tetrafluoro-4-methylbenzyl-(1RS,3RS)-3-[(Z)-2-chloro-3,3,3-trifluoropropyl]-2,2-dimethylcyclopropane carboxylate (tefluthrin) is a pyrethroid pesticide having a broad spectrum of control. In vivo, the activity of tefluthrin is primarily achieved by endocrine or neuroendocrine function following contact and ingestion, which affects sodium channels, thereby interfering with the transmission of nerve impulses. In other words, it permeates into the soil, penetrates insect cuticles, disrupts nerve transmission and causes cessation of food intake and death, thereby providing an additional protection to plants. Tefluthrin is a soil pesticide for controlling soil pests, particularly the pests of orders Coleoptera, Lepitoptera and Diptera, comprising corn rootworms, cutworms, wireworms and white grubs in corns, beets and other crops. However, tefluthrin is a pyrethroid active substance with a high toxicity, particularly against aquatic organisms.

The molecular formula of tefluthrin is as follows:

(I)

Commercial tefluthrin exists in a non-crystalline state and is generally manufactured according to the method described in U.S. Pat. No. 4405640. However, studies have found that after being formulated into a preparation, tefluthrin in a non-crystalline state has a higher toxicity against aquatic organisms. U.S. Pat. No. 2020010403 (A1) discloses a novel crystalline form of tefluthrin, which is referred to as "crystalline form I". The preparation product prepared from the crystalline form I can significantly lower the toxicity of tefluthrin against aquatic organisms. However, the preparation process of the crystalline form is relatively complicated and requires recrystallization of the amorphous product synthesized, resulting in high production costs. From the point of view of environmental protection, there is a continuous need for tefluthrin having lowered toxicity against aquatic organisms.

SUMMARY

To overcome the drawbacks of the prior art, the present application provides a new crystalline form of tefluthrin, which can effectively lower the toxicity of tefluthrin, while having relatively low production costs.

In a first respect, the present invention provides a new crystalline form of 2,3,5,6-tetrafluoro-4-methylbenzyl-(1RS,3RS)-3-[(Z)-2-chloro-3,3,3-trifluoropropyl]-2,2-dimethylcyclopropane carboxylate (tefluthrin), which is referred to as "crystalline form II", wherein an X-ray powder diffraction (X-RPD) pattern recorded by using Cu-Ka radiation at 25° C. of the crystalline form II shows at least 3 (e.g., 3, 4, 5, 6, 7, 8, 9, 10 or 11) of the following reflections at 2θ values in any combination:

$2\theta = 5.35 \pm 0.2°$ (1)

$2\theta = 10.72 \pm 0.2°$ (2)

$2\theta = 10.98 \pm 0.2°$ (3)

$2\theta = 12.52 \pm 0.2°$ (4)

$2\theta = 14.41 \pm 0.2°$ (5)

$2\theta = 18.52 \pm 0.2°$ (6)

$2\theta = 20.00 \pm 0.2°$ (7)

$2\theta = 21.19 \pm 0.2°$ (8)

$2\theta = 21.57 \pm 0.2°$ (9)

$2\theta = 22.13 \pm 0.2°$ (10)

$2\theta = 23.13 \pm 0.2°$ (11)

$2\theta = 25.89 \pm 0.2°$ (12)

$2\theta = 26.19 \pm 0.2°$ (13)

$2\theta = 27.14 \pm 0.2°$ (14)

$2\theta = 28.10 \pm 0.2°$ (15)

$2\theta = 31.13 \pm 0.2°$ (16)

$2\theta = 32.61 \pm 0.2°$ (17)

$2\theta = 34.07 \pm 0.2°$ (18)

$2\theta = 38.26 \pm 0.2°$ (19).

In an embodiment, the X-ray powder diffraction pattern recorded by using Cu-Ka radiation at 25° C. of the crystalline form II of tefluthrin according to the first respect of the present invention shows at least 3, 4, 5 or all of the following reflections at 2θ values in any combination:

$2\theta = 5.35 \pm 0.2°$ (1)

$2\theta = 10.72 \pm 0.2°$ (2)

$2\theta = 10.98 \pm 0.2°$ (3)

$2\theta = 14.41 \pm 0.2°$ (5)

$2\theta = 18.52 \pm 0.2°$ (6)

$2\theta = 20.00 \pm 0.2°$ (7)

$2\theta = 21.19 \pm 0.2°$ (8)

$2\theta = 21.57 \pm 0.2°$ (9)

$2\theta=23.13\pm0.2°$ (11)

$2\theta=25.89\pm0.2°$ (12)

$2\theta=27.14\pm0.2°$ (14).

In another embodiment, the X-ray powder diffraction pattern recorded by using Cu-Kα radiation at 25° C. of the crystalline form II of the tefluthrin shows at least 3 of the following reflections at 2θ values in any combination:

$2\theta=5.35\pm0.2°$ (1)

$2\theta=10.72\pm0.2°$ (2)

$2\theta=10.98\pm0.2°$ (3)

$2\theta=14.41\pm0.2°$ (5)

$2\theta=18.52\pm0.2°$ (6)

$2\theta=20.00\pm0.2°$ (7)

$2\theta=21.19\pm0.2°$ (8)

$2\theta=21.57\pm0.2°$ (9)

$2\theta=23.13\pm0.2°$ (11).

A second object of the present application is to provide a method for preparing the crystalline form II of tefluthrin according to the present invention. Methods for preparing amorphous tefluthrin technical material are known, and the amorphous tefluthrin technical material can be prepared with reference to the process disclosed in U.S. Pat. No. 4405640.

The present application mainly relates to two methods for preparing the crystalline form II of tefluthrin, wherein one method comprises the steps of:

a) washing the tefluthrin-containing reaction solution obtained by chemical synthesis with an acid, water and then a base, and drying same, then removing the solvent by distillation under reduced pressure, and cooling to room temperature to obtain an amorphous tefluthrin; and b) further cooling the amorphous substance obtained in step a) to 5° C. to −24° C., and maintaining the temperature for 0.5-20 hours to obtain the crystalline form II of tefluthrin.

In the above-mentioned preparation method, the operation in step a) is carried out with reference to the post-treatment method in the examples of U.S. Pat. No. 4405640, wherein cooling naturally to room temperature is performed to prevent the precipitation of solid due to local over-cooling and as a result, the unavailability of crystalline form II with a high purity.

In the above-mentioned method for preparing the crystalline form II of tefluthrin, in step b), the amorphous tefluthrin at room temperature obtained in step a) is cooled to 5° C. to −24° C., e.g., 5° C., 3° C., 0° C., −2° C., −4° C., −6° C., −8° C., −10° C., −12° C., −14° C., −16° C., −18° C., −20° C., −22° C., and −24° C., particularly suitably, to the temperature of 0° C. to −15° C., and more particularly suitably to −2° C. to −10° C.

The present invention also provides another method for preparing the crystalline form II of tefluthrin, comprising the specific steps as follows:

a) heating and melting a tefluthrin solid other than the crystalline form II, and then cooling to room temperature; and b) further cooling the amorphous substance obtained in step a) to 5° C. to −24° C., and maintaining the temperature for 0.5-20 hours to obtain the crystalline form II of tefluthrin.

In the above-mentioned method for preparing the crystalline form II of tefluthrin, in step a), the heating and melting is performed at a temperature above the melting point of tefluthrin.

In the above-mentioned method for preparing the crystalline form II of tefluthrin, in step b), the tefluthrin obtained in step a) is cooled to 5° C. to −24° C., e.g., 5° C., 3° C., 0° C., −2° C., −4° C., −6° C., −8° C., −10° C., −12° C., −14° C., −16° C., −18° C., −20° C., −22° C., and −24° C., particularly suitably, to the temperature of 0° C. to −15° C., and more particularly suitably to −2° C. to −10° C.

A third object of the present application is to provide a composition comprising the crystalline form II of tefluthrin according to either the first object or the second object of the present invention and at least one auxiliary.

In a specific embodiment of the third object of the present application, the amount of the crystalline form II of tefluthrin is less than 50% by weight of the composition, more preferably less than 30% by weight of the composition, and particularly suitably less than 3% by weight of the composition.

In a specific embodiment of the third object of the present invention, the composition is in the form of aqueous suspension concentrate (SC), oil dispersion (OD), dispersible concentrate (DC), emulsifiable concentrate (EC), emulsifying seed dressing agent, suspending seed dressing agent, granule (GR), microgranule (MG), suspo-emulsion (SE) and water dispersible granules (WG). The crystalline form II of tefluthrin can be incorporated in a conventional formulation in a known manner using a suitable auxiliary, carrier, solvent etc.

The composition is prepared by mixing the crystalline form II of tefluthrin with at least one auxiliary (e.g., a carrier, a surfactant, a diluent, a wetting agent, a dispersant, any necessary excipient and other formulation components) in a known manner.

The carrier can be precipitated silica (white carbon black), colloidal silica, attapulgite, talc, kaolin or a combination thereof, preferably precipitated silica and kaolin.

The diluent includes, but is not limited to lactose, glucose, fructose, maltose, sucrose in anhydrous or hydrate form, urea, water-soluble or dispersible polymer, water-soluble inorganic salt or a combination thereof. Lactose, starch or a combination thereof is particularly useful for the composition of the present invention.

The wetting agent includes, but is not limited to alkylsulfosuccinate, laurate, alkyl sulfate, phosphate, acetylenic diol, ethoxyl fluoroalcohols, ethoxylated silicone, alkylphenol acetylacetate, phenyl benzenesulfonate, alkyl-substituted benzene sulfonate, alkyl alpha-olefin sulphonate, naphthalenesulfonate, alkyl-substituted naphthalenesulfonates, a condensate of naphthalenesulfonates and alkyl-substituted naphthalenesulfonates with formaldehyde, and alcohol ethoxylate. Sodium alkylnaphthalenesulfonate blend (Morwet EFW) is particularly useful for the composition of the present invention.

The dispersant includes, but is not limited to lignosulfonates (optionally polyethoxylated lignosulfonates) as sodium, calcium and ammonium salts; sodium and ammonium salts of maleic anhydride copolymers; condensed benzenesulfonic acid sodium salts; and modified styrene-acrylic acid polymers and a naphthalenesulfonate-formaldehyde condensate. Notably, the amount of the dispersant is up to 10% by weight of the composition. Modified styrene-acrylic acid polymer (Atlox Metasperse 5505) is particularly useful for the composition of the present invention.

Beneficial Effects of the Present Invention

Compared with the prior art, the present application has the beneficial effects as follows. First of all, in terms of toxicity, the crystalline form II of tefluthrin provided by the present invention avoids the toxicity of the preparations formulated from amorphous tefluthrin against aquatic organisms and has a toxicity comparable to that of crystalline form I reported in the prior art, and in some embodiments, the crystalline form II of tefluthrin shows a toxicity lower than that of crystalline form I. Secondly, in terms of production cost, the amorphous tefluthrin obtained during the synthetic process or the resulting material obtained by heating and melting solid tefluthrin other than the tefluthrin claimed by the present invention can be directly used as a raw material in the preparation of the crystalline form II, and there is no need for adding any solvent and almost no loss of the product, resulting in lower production costs. Finally, in terms of operational complexity, in the preparation of crystalline form I, it is necessary to subject the amorphous technical material to a series of operations such as dissolution, recrystallization, filtration and drying, whereas the preparation of the crystalline form II is more advantageous in terms of saving equipment, raw materials and human resources.

DETAILED DESCRIPTION OF EXAMPLE EMBODIMENTS

Figure 1:
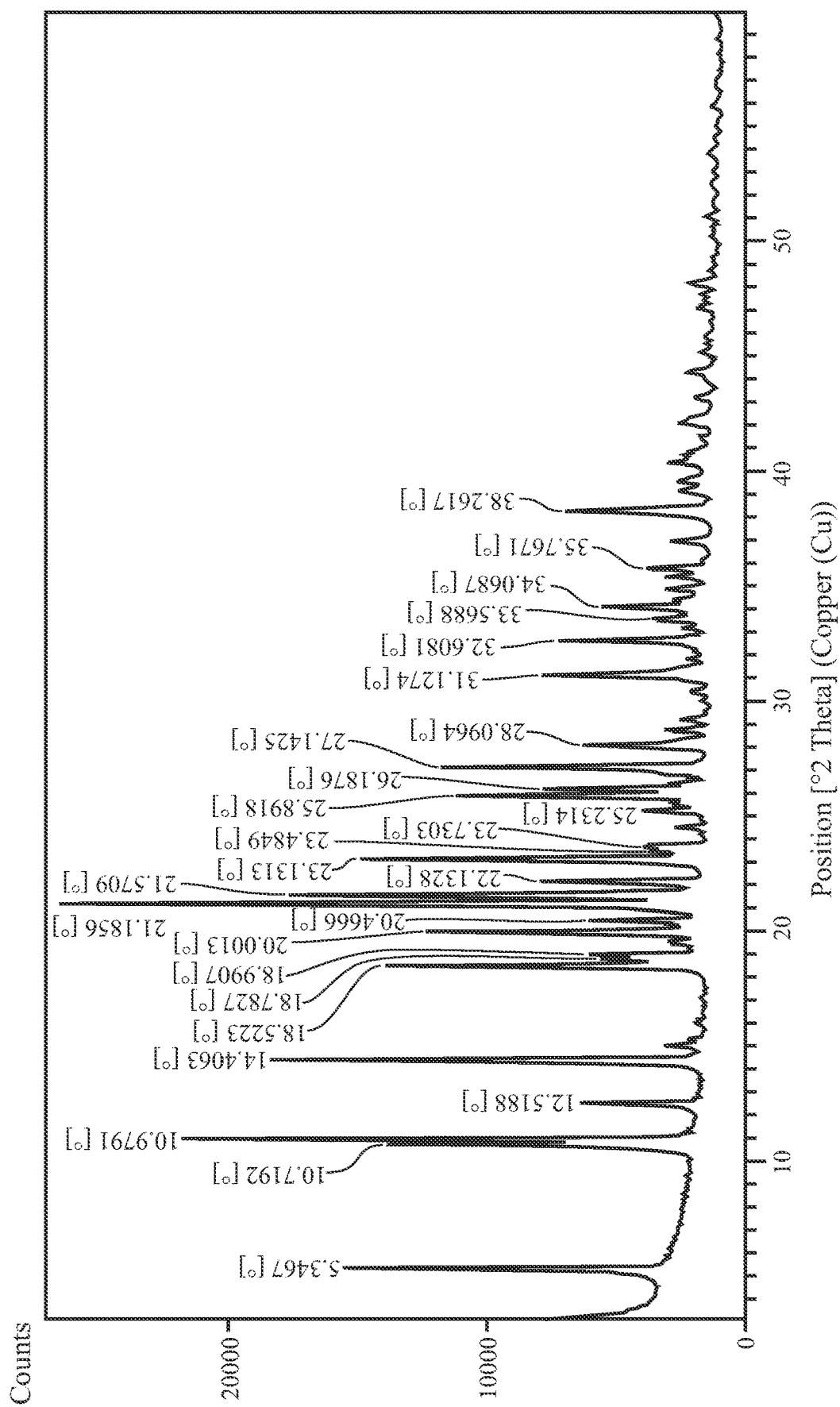
FIG. 1 shows an X-ray powder diffraction pattern of crystalline form II of tefluthrin.

In order to aid the understanding of the present invention, the following examples are set forth for the present invention. A person skilled in the art should be clear that the examples are provided only for aiding the understanding of the present invention but should not be regarded as particular limitations to the present invention.

Example 1: Preparation of Amorphous Tefluthrin

A mixture of thionyl chloride (5.0 ml) and 3-(2-chloro-3,3,3-trifluoro-1-alkenyl)-2,2-dimethylcyclopropane carboxylic acid (50% cis and 50% trans (w/w), 0.242 g) was heated for 5 hours at reflux temperature and maintained at ambient temperature for another 16 hours. After excess thionyl chloride was removed by distillation under reduced pressure (the remaining trace was removed by azeotropic distillation with toluene), the obtained acyl chloride was added into a mixture of 4-methyl-2,3,5,6-tetrafluorobenzyl alcohol (0.24 g), anhydrous pyridine (0.08 g) and anhydrous toluene (10 ml). The obtained mixture was stirred at room temperature for 2 hours and then allowed to stand for another 16 hours at room temperature. After toluene (10 ml) was added, the resulting mixture was sequentially washed with diluted hydrochloric acid (2 N, 20 ml), water and saturated sodium bicarbonate solution, then dried over anhydrous magnesium sulfate and concentrated by distillation under reduced pressure to obtain tefluthrin.

Figure 3:
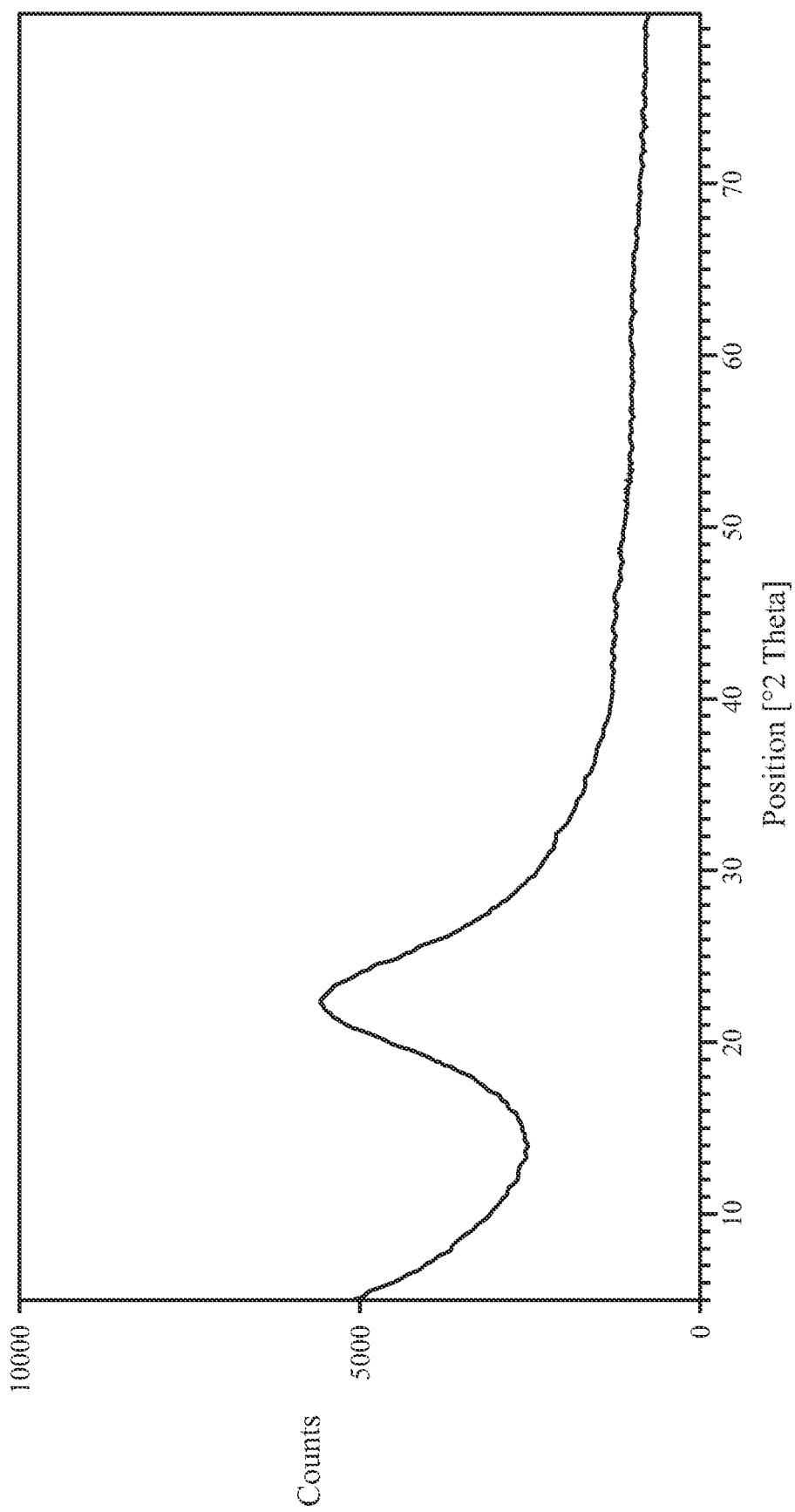
FIG. 3 shows an X-ray powder diffraction pattern of amorphous tefluthrin.

As shown in FIG. 3, no significant signal can be seen in the X-ray powder diffraction pattern of the obtained tefluthrin product, which indicates that the tefluthrin prepared according to the content reported in U.S. Pat. No. 4405640 is amorphous.

Example 2: Preparation of Crystalline Form II of Tefluthrin

Firstly, the amorphous tefluthrin sample (8 g) prepared with reference to example 1 was cooled to room temperature to obtain a light yellow oil. The light yellow liquid was placed in a freezer and frozen while the temperature was kept at −10° C. to −15° C. After about 0.5 hours, a small amount of white solid was precipitated, and the liquid was further frozen for 1-3 hours until the sample was completely cured to obtain 8 g of a white solid.

A sample of the obtained solid tefluthrin was delivered for XRD detection and was found to be crystalline form II of tefluthrin, as shown in FIG. 1.

Reflections are shown in the X-ray powder diffraction pattern of the crystalline form II in FIG. 1 and are summarized in Table 1.

TABLE 1

| 2θ | 2θ | 2θ |
|---|---|---|
| 5.35 ± 0.2° | 21.19 ± 0.2° | 28.10 ± 0.2° |
| 10.72 ± 0.2° | 21.57 ± 0.2° | 31.13 ± 0.2° |
| 10.98 ± 0.2° | 22.13 ± 0.2° | 32.61 ± 0.2° |
| 12.52 ± 0.2° | 23.13 ± 0.2° | 34.07 ± 0.2° |
| 14.41 ± 0.2° | 25.89 ± 0.2° | 38.26 ± 0.2° |
| 18.52 ± 0.2° | 26.19 ± 0.2° | |
| 20.00 ± 0.2° | 27.14 ± 0.2° | |

Example 3: Preparation of Crystalline Form II of Tefluthrin

Commercially available solid tefluthrin other than crystalline form II (15 g) was charged into a three-necked flask. The solid tefluthrin was first slowly warmed to a completely molten state and then naturally cooled to room temperature to obtain a light yellow oil. The light yellow liquid was frozen at 0° C. to −5° C. After about 1.0 hours, a small amount of white solid was precipitated, and the liquid was further frozen for 3-8 hours until the sample was completely cured to obtain 15 g of a white solid.

The white solid was characterized using the XRD powder diffraction as described in example 2 and was determined to be crystalline form II of tefluthrin.

Example 4 Preparation of Crystalline Form I of Tefluthrin
Crystallization from Dimethoxyethane The amorphous tefluthrin sample (10 g) prepared with reference to example 1 and dimethoxyethane (60 ml) were placed in a three-necked round-bottom flask, and the obtained slurry was heated to 70° C. to obtain a uniform solution. The uniform solution was continuously stirred at 70° C. for 2 h; insoluble granules (if any) were filtered; and the solution was slowly cooled to 20° C.-25° C. After cooling, fine crystals were formed, and the heterogeneous mixture obtained was stirred at 20° C. for 2 hours. The slurry was filtered and washed with dimethoxyethane (6 mL). The filtered crystals were dried in vacuo at 20° C. The crystallized product obtained has a purity of about 98% and a crystallization recovery rate of about 85%.

Figure 2:
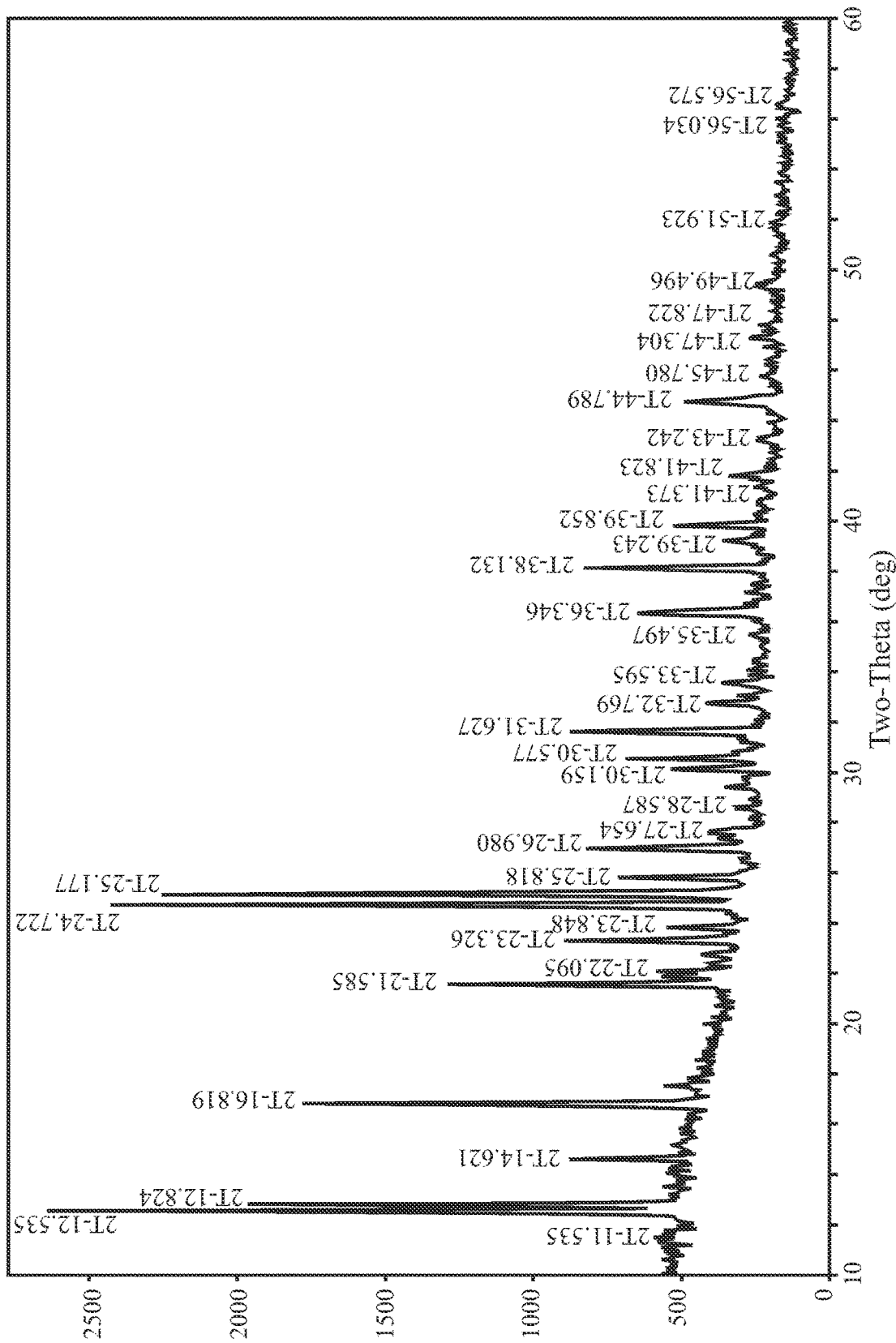
FIG. 2 shows an X-ray powder diffraction pattern of crystalline form I of tefluthrin.

The crystals were characterized using the XRD powder diffraction as described in example 2 and were found to be crystalline form I of tefluthrin, as shown in FIG. 2.

Preparation Examples

Example 5: Preparation of Granule (GR) of 3% Tefluthrin 3.06 g of tefluthrin was mixed with 3.50 white carbon black and then ground to form a first mixture; then 12.0 g of Atlox Metasperse 550S and 6.0 g of Morwet EFW were added into the first mixture to form a second mixture; then 30.0 g of lactose and 45.44 g of kaolin were mixed with the second mixture to form a third mixture; the third mixture was ground to the particle size of 75 micron or less, preferably D100≤30 and D90≤15 μm; the third mixture ground was wet by adding 12.28 g of water and then extruded to form granules; and the granules were dried to a temperature below the melting point of tefluthrin to prepare an agricultural pesticide preparation.

TABLE 2

| Content | Weight % | | | Function |
|---|---|---|---|---|
| Amorphous tefluthrin, 98% (prepared in example 1) | 3.06 | 0 | 0 | Active ingredient |
| Crystalline form II of tefluthrin, 98% (prepared in example 2) | 0 | 3.06 | 0 | Active ingredient |
| Crystalline form 1 of tefluthrin, 98% (prepared in example 4) | 0 | 0 | 3.06 | Active ingredient |
| White carbon black (precipitated silica) | 3.5 | 3.5 | 3.5 | Carrier |
| Modified styrene-acrylic acid polymer (Atlox Metasperse 550S) | 12.0 | 12.0 | 12.0 | Dispersant |
| Sodium alkylnaphthalenesulfonate blend (Morwet-EFW) | 6 | 6 | 6 | Wetting agent |
| Lactose | 30 | 30 | 30 | Diluent |
| Kaolin | 45.44 | 45.44 | 45.44 | Diluent |

Example 6: Preparation of Granule (GR) of 5% Tefluthrin 5.10 g of tefluthrin was mixed with 3.50 g of white carbon black and then ground to form a first mixture; then 10.0 g of Atlox Metasperse 550S and 6.0 g of Morwet EFW were added into the first mixture to form a second mixture; then 30.0 g of lactose and 45.4 g of kaolin were mixed with the second mixture to form a third mixture; the third mixture was ground to the particle size of 75 micron or less, preferably D100≤30 and D90≤15 m; the third mixture ground was wet by adding 12.28 g of water and then extruded to form granules; and the granules were dried to a temperature below the melting point of pesticides to prepare an agricultural pesticide preparation.

TABLE 3

| Content | Weight % | | | Function |
|---|---|---|---|---|
| Amorphous tefluthrin, 98% (prepared in example 1) | 5.10 | 0 | 0 | Active ingredient |
| Crystalline form II of tefluthrin, 98% (prepared in example 2) | 0 | 5.10 | 0 | Active ingredient |
| Crystalline form 1 of tefluthrin, 98% (prepared in example 4) | 0 | 0 | 5.10 | Active ingredient |
| White carbon black (precipitated silica) | 3.5 | 3.5 | 3.5 | Carrier |
| Modified styrene-acrylic acid polymer (Atlox Metasperse 550S) | 10.0 | 10.0 | 10.0 | Dispersant |
| Sodium alkylnaphthalenesulfonate blend (Morwet-EFW) | 6 | 6 | 6 | Wetting agent |
| Lactose | 30 | 30 | 30 | Diluent |
| Kaolin | 45.4 | 45.4 | 45.4 | Diluent |

Example 7 Toxicity Test
Sample Preparation

Stock solutions (1 g/L) in dimethyl sulfoxide (DMSO) were prepared using the samples prepared in examples 5 and 6. Serial dilutions of the stock solutions in DMSO were prepared at a final concentration of 0.5 mol/L. The concentration is expressed as nominal values.

Culture and Preparation of Marine Copepods

Copepods (A. clausi) were retained in a culture vessel (2.5 L plastic bucket) and maintained in a temperature-controlled room at 14° C.±11° C. under dim light with a photoperiod of 14 hours light and 10 hours dark.

Acute Toxicity Test

Adult marine copepods were used as research objects, and a 48-hour static renewal test was carried out to study the acute toxicity against marine copepods of the tefluthrin prepared according to different formulas in example 5 and example 6. In a series of tests, adult marine copepods were exposed to 5 different concentrations, and for control, the test for each concentration was performed in triplicate with 10 animals. The animals were transferred into the test solutions using a disposable Pasteur pipette, and dilution was reduced by minimal addition of seawater. Containers for exposure were 50 mL borosilicate glass beakers containing 40 mL of the test solutions. The tests were carried out in a temperature-controlled room (14° C.±1° C.) under a dim fluorescent lamp with a photoperiod of 14 hours light and 10 hours dark. The endpoint of the test was inanimation, and when the animals showed no animation if gently poked with water flow or blown, they can be determined as inanimate. The motility of the animals was observed under a stereoscopic microscope after 48 hours. If the survival rate of the control group was more than 90%, then the test was considered to be successful.

The acute LC50 values were calculated using Probit or Spearman-Karber analysis (using Tox Calc).

Results

TABLE 4

| Sample | LC50 (g/L) |
|---|---|
| Example 5 Amorphous tefluthrin | 0.69 |
| Example 5 Crystalline form II of tefluthrin | 6.00 |

TABLE 4-continued

| Sample | LC50 (g/L) |
|---|---|
| Example 5 Crystalline form I of tefluthrin | 5.30 |
| Example 6 Amorphous tefluthrin | 0.53 |
| Example 6 Crystalline form II of tefluthrin | 4.20 |
| Example 6 Crystalline form I of tefluthrin | 3.72 |

According to the experimental results, it is surprisingly found that the toxicity of the crystalline form II of tefluthrin is much lower than that of the amorphous form, and even lower than that of the crystalline form I. For this reason, the crystalline form II of tefluthrin can be highly suitable for preparing commercial preparations.

What is claimed is:

1. A crystalline form II of 2,3,5,6-tetrafluoro-4-methyl-benzyl-(1RS,3RS)-3-[(Z)-2-chloro-3,3,3-trifluoroprop-1-enyl]-2,2-dimethylcyclopropane carboxylate (tefluthrin), wherein an X-ray powder diffraction pattern recorded by using Cu-Ka radiation at 25° C. of the crystalline form II shows at least 3 of the following reflections at 2θ values in any combination:

$2\theta=5.35\pm0.2°$ (1)

$2\theta=10.72\pm0.2°$ (2)

$2\theta=10.98\pm0.2°$ (3)

$2\theta=12.52\pm0.2°$ (4)

$2\theta=14.41\pm0.2°$ (5)

$2\theta=18.52\pm0.2°$ (6)

$2\theta=20.00\pm0.2°$ (7)

$2\theta=21.19\pm0.2°$ (8)

$2\theta=21.57\pm0.2°$ (9)

$2\theta=22.13\pm0.2°$ (10)

$2\theta=23.13\pm0.2°$ (11)

$2\theta=25.89\pm0.2°$ (12)

$2\theta=26.19\pm0.2°$ (13)

$2\theta=27.14\pm0.2°$ (14)

$2\theta=28.10\pm0.2°$ (15)

$2\theta=31.13\pm0.2°$ (16)

$2\theta=32.61\pm0.2°$ (17)

$2\theta=34.07\pm0.2°$ (18)

$2\theta=38.26\pm0.2°$ (19).

2. The crystalline form II of tefluthrin according to claim 1, wherein the X-ray powder diffraction pattern recorded by using Cu-Ka radiation at 25° C. of the crystalline form shows at least 3 of the following reflections at 2θ values in any combination:

$2\theta=5.35\pm0.2°$ (1)

$2\theta=10.72\pm0.2°$ (2)

$2\theta=10.98\pm0.2°$ (3)

$2\theta=12.52\pm0.2°$ (4)

$2\theta=14.41\pm0.2°$ (5)

$2\theta=18.52\pm0.2°$ (6)

$2\theta=20.00\pm0.2°$ (7)

$2\theta=21.19\pm0.2°$ (8)

$2\theta=21.57\pm0.2°$ (9)

$2\theta=23.13\pm0.2°$ (11)

$2\theta=25.89\pm0.2°$ (12)

$2\theta=27.14\pm0.2°$ (14).

3. The crystalline form II of tefluthrin according to claim 2, wherein the X-ray powder diffraction pattern recorded by using Cu-Ka radiation at 25° C. shows at least 3 of the following reflections at 2θ values in any combination:

$2\theta=5.35\pm0.2°$ (1)

$2\theta=10.72\pm0.2°$ (2)

$2\theta=10.98\pm0.2°$ (3)

$2\theta=14.41\pm0.2°$ (5)

$2\theta=18.52\pm0.2°$ (6)

$2\theta=20.00\pm0.2°$ (7)

$2\theta=21.19\pm0.2°$ (8)

$2\theta=21.57\pm0.2°$ (9)

$2\theta=23.13\pm0.2°$ (11).

4. A method for preparing the crystalline form II of tefluthrin according to claim 1, comprising the steps of:
   a) washing the reaction solution obtained by synthesizing tefluthrin with an acid, water and then a base, and drying same, then removing the solvent by distillation under reduced pressure, and cooling to room temperature to obtain an amorphous tefluthrin; and
   b) further cooling the amorphous substance obtained in step a) to 5° C. to −24° C., and maintaining the temperature for 0.5-20 hours to obtain the crystalline form II of tefluthrin.

5. The method according to claim 4, wherein in step a), the cooling to room temperature is cooling naturally to room temperature.

6. The method according to claim 4, wherein in step b), the cooling of the tefluthrin at room temperature obtained in step a) to 5° C. to −24° C. is cooling the tefluthrin at room temperature obtained in step a) to 0° C. to −15° C.

7. A method for preparing the crystalline form II of tefluthrin according to claim 1, comprising the steps of:
   a) heating and melting a tefluthrin solid other than the crystalline form II, and then cooling to room temperature; and
   b) further cooling the amorphous substance obtained in step a) to 5° C. to −24° C., and maintaining the temperature for 0.5-20 hours to obtain the crystalline form II of tefluthrin.

8. The method according to claim 7, wherein in step a), the heating and melting is performed at a temperature above the melting point of tefluthrin.

9. The method according to claim 7, wherein in step b), the cooling of the tefluthrin at room temperature obtained in step a) to 5° C. to −24° C. is cooling the tefluthrin at room temperature obtained in step a) to 0° C. to −15° C.

10. A formulation, wherein the composition comprises the crystalline form II of tefluthrin according to claim 1 and at least one auxiliary.

11. The method according to claim 6, wherein in step b), the cooling of the tefluthrin at room temperature obtained in step a) to 5° C. to −24° C. is cooling the tefluthrin at room temperature obtained in step a) to −2° C. to −10° C.

12. The method according to claim 9, wherein in step b), the cooling of the tefluthrin at room temperature obtained in step a) to 5° C. to −24° C. is cooling the tefluthrin at room temperature obtained in step a) to −2° C. to −10° C.

* * * * *